United States Patent [19]

Leonard et al.

[11] Patent Number: 4,468,523

[45] Date of Patent: Aug. 28, 1984

[54] SYNTHESIS OF DIALKYL OXALATES BY THE HETEROGENEOUSLY CATALYZED OXIDATIVE CARBONYLATION OF ALCOHOLS

[75] Inventors: John J. Leonard, Springfield; John A. Sofranko, West Chester, both of Pa.

[73] Assignee: Atlantic Richfield Company, Los Angeles, Calif.

[21] Appl. No.: 388,855

[22] Filed: Jun. 16, 1982

[51] Int. Cl.³ .............................................. C07C 67/36
[52] U.S. Cl. ...................... 560/204; 502/74; 502/170; 502/182; 502/185; 502/230; 502/242; 502/247; 502/262; 502/326; 502/350; 502/353; 560/190
[58] Field of Search ............... 560/204, 190; 252/461, 252/472, 454, 456, 460; 502/74, 182, 185, 230, 242, 247, 262, 326, 350, 353, 170

[56] References Cited

U.S. PATENT DOCUMENTS

| | | | |
|---|---|---|---|
| 3,393,136 | 7/1968 | Fenton et al. | 560/204 |
| 3,994,960 | 11/1976 | Yamazaki et al. | 560/204 |
| 4,005,129 | 1/1977 | Zehner | 560/204 |
| 4,005,130 | 1/1977 | Zehner | 560/204 |
| 4,076,949 | 2/1978 | Zehner | 560/204 |
| 4,118,589 | 10/1978 | Cassar et al. | 560/204 |
| 4,281,174 | 7/1981 | Current | 560/204 |

FOREIGN PATENT DOCUMENTS 51-29428 12/1976 Japan.

Primary Examiner—Natalie Trousof
Assistant Examiner—Vera C. Clarke
Attorney, Agent, or Firm—Delbert E. McCaslin

[57] ABSTRACT

Synthesis of dialkyl oxalates by the oxidative carbonylation of liquid monohydric saturated alcohols of from 1 to 20 carbon atoms with carbon monoxide and oxygen or an oxygen-containing gas in the presence of a catalytic amount of a catalyst comprising palladium or a salt thereof in combination with vanadium in the oxide ($V_2O_5$, $V_2O_4$, $V_2O_3$) form and titanium or a non-hydrolyzable salt thereof, said catalyst being present in a heterogeneous phase.

14 Claims, No Drawings

SYNTHESIS OF DIALKYL OXALATES BY THE HETEROGENEOUSLY CATALYZED OXIDATIVE CARBONYLATION OF ALCOHOLS

BACKGROUND OF THE INVENTION

The preparation of dialkyl oxalate esters by the homogeneous catalyzed oxidative carbonylation of alcohols in the presence of metal salt catalysts, redox agents, dehydrating agents and other compounds such as amines, carbonates, nitrates, hydroxides and ureas is well known. An article by Donald M. Fenton and Paul J. Steinwand, Journ. of Org. Chem., Vol. 39, Nos. 5, 1974, pp. 701–704 describes a general mechanism for the oxidative carbonylation of alcohols to yield dialkyl oxalates using a palladium redox system, oxygen and dehydrating agents. Typical prior art patents disclosing homogeneous catalyzed oxidative carbonylation of alcohols to prepare oxalate esters are U.S. Pat. Ser. Nos. 3,393,136; 3,994,960; 4,005,129; 4,005,130; 4,076,949; 4,118,589 and 4,281,174 as well as West German Patent No. 2,213,435 and West German Offenlegungschrift No. 2,601,139.

The present invention provides a much improved process for the production of dialkyl oxalates by employing an insoluble easily recoverable heterogeneous catalyst for the oxidative carbonylation of alcohols.

U.S. Pat. Ser. No. 4,229,591 describes a process for the preparation of a diester of oxalic acid by contacting an ester of nitrous acid or an alcohol and a nitrogen oxide or hydrate thereof in the gaseous phase in the presence of a solid catalyst containing palladium or a salt thereof such as palladium on activated carbon.

Japanese Kokai 75-157,311 discloses the preparation of oxalic acid esters by reacting a $C_1$ to $C_{20}$ monohydric alcohol, carbon monoxide and molecular oxygen in the presence of a supported Group VIII metal and a Group IB, IIB, III, IV, V, VI, and VIIIB metal, aluminum, iron, cobalt or nickel.

U.S. Pat. Ser. No. 4,039,572 discloses the preparation of diesters of dicarboxylic acids by the oxidative carbonylation of olefins and alcohols using a carrier supported catalyst consisting of (1) a platinum group metal compound and (2) a compound of a metal having an atomic number of not less than 22 which has been reduced to a metal and has a ratio of (2) to (1) of from 0.0005:1 to 10:1 gram atoms.

The oxalate products of this invention have many commercial applications and are used as solvents, dye intermediates, for the preparation of pharmaceuticals as well as feedstock for hydrogenation to ethylene glycol by, for example, the process described in U.S. Pat. Ser. No. 4,112,245.

SUMMARY OF THE INVENTION

In accordance with the present invention there is provided a superior improved process for the synthesis of dialkyl oxalates by the liquid or vapor phase oxidative carbonylation of a normally liquid alcohol with a mixture of carbon monoxide and oxygen in the presence of a catalytic amount of an insoluble heterogeneous catalyst comprising (1) palladium metal or a salt thereof, (2) vanadium in the oxide form, and (3) titanium metal or a non-hydrolyzable salt thereof. High yield and selectivity of dialkyl oxalates is obtained especially with the lower alcohols. In addition, the Pd-V-Ti catalyst combination may be supported on, for example silica ($SiO_2$) to provide still greater selectivity and catalyst productivity.

It is a primary object of this invention to provide a process for the preparation of dialkyl oxalates in high yield and high conversion of reactants employing an improved heterogeneous catalyst system.

It is a further object of this invention to provide a specific heterogeneous catalytic mechanism for the employment of palladium or salts thereof, vanadium oxides and titanium or non-hydrolyzable salts thereof in an oxidative carbonylation process employing alcohol, carbon monoxide and oxygen as reactants.

These and other objects and advantages of this invention will become apparent from the description of the invention which follows and from the claims.

DESCRIPTION OF THE INVENTION

The present invention is based on the discovery that superior yields of dialkyl oxalates at improved selectivities and catalyst productivity can be obtained from the reaction of an alcohol and a mixture of carbon monoxide, oxygen or an oxygen containing gas, such as air, at elevated temperatures and pressures in the presence of a solid catalytic mixture of palladium or a salt thereof, vanadium in the form of its oxide and titanium metal or a non-hydrolyzable salt thereof. The Pd-V-Ti catalyst mixture employed is in the heterogeneous state in the reaction at reaction conditions and while vapor phase reactions employing a bed of catalyst may be employed the reactions are generally carried out with a slurry of the catalyst mixture, supported or unsupported, in the reactant alcohol. The catalyst combination may also be on inert support materials such as alumina, silica gel, aluminosilicates, activated carbon or zeolites, and when so employed generally provide a higher percent selectivity of product and greater catalyst productivity.

The reaction between the alcohol, carbon monoxide, and oxygen may be carried out in an autoclave or any other high pressure reactor. Although the order of addition of reactants and the catalyst mixture may vary, a general procedure is to charge the alcohol and catalyst (supported or unsupported) into the reaction vessel, and then introduce the proper amount of carbon monoxide and oxygen to the desired reaction pressure and then heat the mixture to the desired temperature for the appropriate period. The reaction can be carried out batchwise or as a continuous process and the order of addition of the reactants may also be varied to suit the particular apparatus employed. The addition of the oxygen or oxygen-containing gas, such as air, can be a pulsed or continuous addition to the reaction system. The reaction products are recovered and treated by any conventional method such as distillation and/or filtration, etc. to effect separation of the oxalate ester from unreacted materials, catalyst, by-products, etc.

The alcohols which may be employed in concentrations of from about 50 to 99.7 weight percent, preferably 77 to 94 weight percent and suitable for use in the process of the present invention can be monohydric saturated aliphatic and alicyclic alcohols and may contain other substitutents such as amido, alkoxy, amino, carboxy, cyano, etc. radicals in addition to the hydroxyl group. The substituents, in general, do not interfere with the reaction of the invention.

The alcohols which are employed may be primary, secondary, or tertiary alcohols and conform to the general formula ROH, wherein R is an optionally substituted aliphatic, or alicyclic group containing from 1 to 20 carbon atoms and preferably unsubstituted aliphatic alcohols containing from 1 to 10 carbon atoms and more preferably 1 to 4 carbon atoms. In general, the alcohol is one which is normally liquid under the conditions employed in the carboxylation reaction. Representative alcohols especially suitable for use in this invention are saturated monohydric alcohols such as methyl, ethyl, n-, iso-, sec-, and tert-butyl, amyl, hexyl, octyl, lauryl, n- and isopropyl, cetyl, benzyl, chlorobenzyl and methoxy-benzyl alcohols as well as for example, cyclohexanol, heptanols, decanols, undecanols, 2-ethyl hexanol, nonanol, myristyl alcohol, stearyl alcohol, methyl cyclohexnol, pentadecanol, oleyl and eicosonyl alcohols, and the like. The preferred alcohols are the primary and secondary monohydric saturated aliphatic alcohols, such as methanol, ethanol, 1- and 2-propanol, n-butyl alcohol etc., up to 10 carbon atoms.

The palladium salts which may be employed in the process of this invention and in forming the catalyst mixture include the palladium (II) compounds or mixtures thereof. Among the chemical forms of the palladium compounds which can be used as such or as mixtures are the palladium halides, sulfates, carboxylates, acetates, oxides, and nitrates, preferably the palladium (II) halides. Representative palladium salt compounds include, for example palladium (II) oxide, palladium (II) chloride, palladium (II) sulfate, palladium (II) acetate, palladium (II) iodide, palladium (II) oxalate, palladium (II) propionate, etc. The palladium content of the catalyst system may range from about 0.25 to 5 weight percent on the V/Ti as their oxides.

The vanadium employed in the catalyst mixture is in the essentially insoluble oxide form and may be $V_2O_5$, $V_2O_4$ or $V_2O_3$ or mixture thereof. Soluble vanadium compounds cannot be employed as they over oxidize the reaction and inhibit selectivity.

The titanium salts which may be employed in the process of this invention and in forming the catalyst mixture include the non-hydrolyzable titanium salts such as titanium di- and trioxide, titanium oxalate, titanium and titanous sulfate and titanyl acetylacetonate, etc. It is critical that the titanium compound be non-hydrolyzable as hydrolyzable compounds such as $TiC_4$ will react with water and the reactant alcohol making them unsatisfactory.

While a method for the preparation of the Pd-V-Ti supported or unsupported catalyst is set forth hereinafter in the examples, other ordinary methods for the preparation of such catalyst mixture may be used as long as they produce a Pd-V-Ti catalyst having an appropriate ratio of one metal to the other. Generally, the ratio of the Pd to the V to Ti metals in the catalyst employed will range from about 0.01:1:1 to about 0.2:1:1 on a weight percent basis. The reaction is generally carried out in the presence of a catalytic proportion of the catalyst combination and will proceed with small amounts of the catalyst hereinabove described. Generally the proportions of catalyst used in the reaction will be equivalent to between about 0.001 to 5 weight percent of the alcohol employed and are preferably employed in amounts of between 0.01 to 2 percent by weight of the alcohol employed.

Although not required, solvents, if desired, which are chemically inert to the components of the reaction system may be employed. Suitable solvents include, for example, hydrocarbons such as hexane, heptane, toluene and xylene; ethers such as tetrahydrofuran, diethylether, diphenylether; halogenated hydrocarbons such as methylene chloride, chlorobenzene and dichlorobenzene; organic esters such as ethyl acetate, n-propyl formate, isopropyl acetate, sec- and iso-butyl acetate, amyl acetate, cyclohexyl acetate, n-propyl benzoate; lower alkyl phthalates, etc. and the alkyl sulfones and sulfoxides such as propylene ethyl sulfoxide, diisopropyl sulfone, diisooctyl sulfoxide, acetone, cyclohexanone, etc.

As indicated above the reaction can be suitably performed by introducing the oxygen and carbon monoxide at a desired pressure into contact with the alcohol/catalyst mixture comprising the palladium-vanadium oxide-titanium catalyst either supported or unsupported and heating to the desired temperature. In general, a carbon monoxide pressure of about 400 psig to about 5000 psig partial pressure and preferably from 900 psig to about 2200 psig is employed. Stoichiometric quantities of carbon monoxide are generally employed. However, an excess of carbon monoxide may be employed, for example, in continuous processes where large excess of or high carbon monoxide requirements are generally utilized, a suitable recycle of the unreacted carbon monoxide may be employed. The reaction will proceed at temperatures of from about 40° C. to 150° C. It is generally preferred to operate the process at temperatures in the range of 75° C. to 120° C. to obtain a convenient rate of reaction. Heating and/or cooling means may be employed interior and/or exterior of the reaction to maintain the temperature within the desired range At least stoichiometric amounts of oxygen or an oxygen-containing gas such as air may be employed and at any oxygen partial pressure such that the explosive range is avoided. Thus, the concentrations of oxygen should be low enough so that the reaction mixture is not potentially explosive. The Handbook of Chemistry and Physics, 48th Edition, 1967 indicates that the explosive limits of pure oxygen in carbon monoxide is 6.1 to 84.5 volume percent and air in carbon monoxide to be 25.8 to 87.5 volume percent. The volume percent of the oxygen in the oxygen-carbon monoxide mixture usually amounts to about 3 to 6 percent. In carrying out the reaction the oxygen is charged to the reaction vessel to the desired pressure and concentration and may be charged in portions for safety reasons. Total carbon monoxide-oxygen pressures will range between about 500 psig and 6000 psig.

The reaction time is generally dependent upon the alcohol being reacted, temperature, pressure and on the amount of the catalyst mixture being charged as well as the type of equipment being employed. Reaction times will vary dependent on whether the process is continuous or batch but will generally run for from 0.5 to 2 hours under batch conditions. The reaction is limited by the available alcohol and carbon monoxide.

The following examples are provided to illustrate the invention in accordance with the principles of this invention but are not to be construed as limiting the invention in any way except as indicated by the appended claims.

EXAMPLE 1

Preparation of a Pd-V-Ti Catalyst 133 g. of vanadium pentoxide was added to a solution prepared from 635 ml of concentrated hydrochloric acid and 340 ml of water and stirred until a homogeneous solution formed. To this solution, 277 g. of titanium tetrachloride was added slowly over a 2 hour period while maintaining the temperature below 40° C. in an inert nitrogen environment. This vanadium-titaninium solution was then added concurrently with 700 ml of an 8 percent solution of ammonium hydroxide solution to 450 ml of water which was cooled in an ice/water bath. The pH of the resulting solution was maintained at 1.4 to 2.0 during the addition of the vanadium-titanium total solution. The pH of the solution was then adjusted to a pH of 5.7, the mixture filtered and the solids thoroughly washed with water and dried at 80° C. in a vacuum oven. The solid was calcined in air at 400° C. for 16 hours to give a vanadium oxide/titanium oxide material. 15.0 g. of the vanadium-titanium solid material was added to 30 ml of a 1N ammonium hydroxide solution which contained 0.625 g. of palladium chloride in solution. This mixture was allowed to stand for 1 hour and then dried at 90° C. in a vacuum oven. The resulting solid was calcined at 400° C. in air for 16 hours to yield a $Pd-V_2O_5-TiO_2$ solid catalyst containing as the metal 2.5 percent Pd, 27 percent V and 26 percent Ti.

A $SiO_2$ supported $Pd-V_2O_5-TiO_2$ catalyst was prepared in accordance with the above procedure by adding 1940 g. of silica gel to 2000 ml of cooled water prior to the concurrent addition of the V-Ti solution and 8 percent solution of ammonium hydroxide to give a catalyst containing as the metal 1 percent Pd, 4 percent V and 4 percent Ti on silica.

EXAMPLE 2 (Comparative)

To a 500 cc stainless steel stirred autoclave was charged 200 g. of methanol and 2.5 g. of a palladium-vanadium oxide catalyst (1 percent Pd and 56 percent V as the metal). The autoclave was brought to a temperature of 100° C. and 1200 psig of carbon monoxide added with stirring. 400 psig air was charged and then 900 psig carbon monoxide to bring the total pressure to 2500 psig. The reaction was carried out for 1 hour after which the reactor was cooled to ambient temperature and vented to ambient pressure and gas samples obtained. Solids were separated from liquid products by vacuum filtration. The liquid product was analyzed by gas-liquid chromatography (glc) and titration methods and the gaseous product was analyzed by gas chromatograph. Analysis of the products showed 4.86 mmole dimethyl oxalate, 12.6 mmole methyl formate and 0.6 mmole carbon dioxide. Selectivity to dimethyl oxalate was 42.4 percent with a catalyst productivity of 0.573 g/g-hr.

EXAMPLE 3 (Comparative)

The procedure of Example 2 was repeated using 1 g. of a $V_2O_5-TiO_2$ catalyst with no palladium content. The reaction was carried out for 1 hour under the same temperature and pressures of Example 2. Analysis of the reaction products showed 1.12 mmole of dimethyl oxalate, 0.52 mmole methyl formate and 0.3 mmole carbon dioxide with a selectivity to dimethyl oxalate of 57.7 percent and a catalyst productivity of 0.13 g/g-hr.

EXAMPLE 4

The procedure and operating conditions (time, temperature and gas pressures) of Example 2 was repeated using 1.0 g. of unsupported catalyst prepared as in Example 1. Analysis of the reaction products showed 23.8 mmole dimethyl oxalate, 8.05 mmole methyl formate and 1.58 mmole of carbon dioxide. Selectivity to dimethyl oxalate was 83.2 percent with a catalyst productivity of 2.81 g/g-hr.

EXAMPLES 5 to 14

In Examples 5 to 14 which follow in table form, the procedure and general operating conditions as employed in Example 2 was repeated using 2.5 g. of various catalysts either supported or unsupported, alcohol, reactants, time of reaction, and temperatures. Total pressures were 2100 psig CO and 400 psig $O_2$. Products were analyzed by gas-liquid chromatography and titration to give mole percent selectivity to the dialkyl oxalate and catalyst productivity in gram/gram-hour. Examples 5 and 6 are comparative examples.

TABLE

| Ex. No. | Catalyst (% by wt. metal) | Temp. °C. | Time hrs. | Alcohol (gms.) | Co—Solvent (gms.) | Selectivity to Dialkyl Oxalate (mole %) | Catalyst Productivity (g/g-hr.) |
| --- | --- | --- | --- | --- | --- | --- | --- |
| 5 | Pd(2.0) on silica | 100 | 1.0 | methanol (200 g.) | — | 35.7 | 0.18 |
| 6 | Pd(2.0) on $SiO_2$[1] | 100 | 1.0 | methanol (200 g.) | — | 16.2 | 0.10 |
| 7 | Pd(1.0)—V(4.0)—Ti(4.0)[2] on $SiO_2$ | 100 | 1.0 | methanol (200 g.) | — | 87.3 | 2.62 |
| 8 | Pd(1.0)—V(27.0)—Ti(26.0)[2] | 75 | 0.25 | n-butanol (200 g.) | — | 30.0 | 0.53 |
| 9 | Pd(1.0)—V(27.0)-Ti(26.0)[2] | 125 | 0.25 | methanol (100 g.) | diphenyl ether (100 g.) | 57.5 | 0.48 |
| 10 | Pd(1.0)—V(4.0)—Ti(4.0)[2] on $SiO_2$ | 120 | 0.50 | decanol (100 g.) | chlorobenzene (100 g.) | 60.1 | 0.72 |
| 11 | Pd(1.0)—V(27.0)—Ti(25.0)[3] | 100 | 1.0 | methanol (200 g.) | — | 56.0 | 1.18 |
| 12 | Pd(3.0)—V(27.0)—Ti(26.0)[2] | 100 | 1.0 | n-butanol (200 g.) | — | 40.0 | 0.54 |
| 13 | Pd(3.0)—V(27.0)—Ti(26.0)[2] | 100 | 1.0 | ethanol (200 g.) | — | 66.0 | 1.87 |
| 14 | Pd(3.0)—V(27.0)—Ti(26.0)[2] | 100 | 1.0 | n-propanol (200 g.) | — | 49.0 | 0.90 |

[1]Slurry charged in Example 6 contained 0.1% soluble vanadium oxalate.
[2]Vanadium as $V_2O_5$ and Ti as $TiO_2$.
[3]Vanadium as $V_2O_5$ and Ti as $Ti_2(C_2O_4)_3$.

We claim:
1. A process for the preparation of dialkyl oxalates by the oxidative carbonylation of a liquid saturated monohydric aliphatic or alicyclic alcohol containing from 1 to 20 carbon atoms with a mixture of carbon monoxide and oxygen or an oxygen-containing gas at a tempera- ture of from about 40° C. to 150° C. and a total pressure of between about 500 psig and 6000 psig in the presence of an essentially insoluble hetrogeneous tri-metallic-containing catalyst comprising a solid mixture of (1) palladium metal or a salt thereof, (2) vanadium in the form of its oxide, and (3) titanium metal or a non-hydrolyzable salt thereof, said catalyst containing as the metal on a weight percent basis palladium, vanadium and titanium in the range of from about .01:1:1 to about 0.2:1:1 respectively, and recovering the desired dialkyl oxalate.

2. A process according to claim 1 wherein the alcohol is a monohydric aliphatic alcohol containing from 1 to 10 carbon atoms.

3. A process according to claim 2 wherein the alcohol is selected from the group consisting of methanol, ethanol, propanol, butanol and decanol.

4. A process according to claim 3 wherein the alcohol is methanol.

5. A process according to claim 3 wherein the alcohol is ethanol.

6. A process according to claim 1 wherein the vanadium in the catalyst is in the form of $V_2O_5$.

7. A process according to claim 1 wherein the titanium in the catalyst is in the form of $TiO_2$.

8. A process according to claim 1 wherein the Pd-V-Ti catalyst is employed in amounts of from about 0.001 to 5 weight percent based on the alcohols.

9. A process according to claim 8 wherein between 0.01 to 2 percent by weight catalyst is employed based on the alcohol.

10. A process according to claim 1 wherein the temperature is between about 75° C. and 120° C. and the carbon monoxide partial pressure is between 900 psig and 2200 psig.

11. A process according to claim 1 wherein the reaction is carried out a solvent inert to the components of the reaction system.

12. A process according to claim 1 wherein the heterogeneous Pd-V-Ti containing catalyst is supported.

13. A process according to claim 12 wherein the support is $SiO_2$.

14. A process for the preparation of dimethyl oxalate by the oxidative carbonylation of methanol with carbon monoxide and oxygen or an oxygen-containing gas at a temperature of from 75° C. to 120° C. and a carbon monoxide pressure of 2100 psig and oxygen pressure of 400 psig in the presence of a tri-metallic-containing solid catalyst mixture consisting of palladium metal, vandium pentoxide and titanium dioxide said catalyst containing as the metal on a weight percent basis palladium, vanadium and titanium in the range of from about 0.01:1:1 to 0.2:1:1 respectively and being present in the heterogeneous phase.

* * * * *